United States Patent [19]

Crounse

[11] 4,028,357
[45] June 7, 1977

[54] 2'-(4,6-DISUBSTITUTED)-s-TRIAZIN-2-YL)AMINO-6'-DIALKYLAMINO FLURANS

[75] Inventor: Nathan Norman Crounse, Cincinnati, Ohio

[73] Assignee: Sterling Drug Inc., New York, N.Y.

[22] Filed: July 31, 1975

[21] Appl. No.: 600,773

[52] U.S. Cl. .................. 260/249.5; 260/249.6; 260/249.8

[51] Int. Cl.² ............ C07D 251/44; C07D 251/50; C07D 251/70

[58] Field of Search .......... 260/249.5, 249.6, 249.8

[56] References Cited

UNITED STATES PATENTS

| | | | |
|---|---|---|---|
| 3,183,231 | 5/1965 | Buell | 260/249.6 |
| 3,867,383 | 2/1975 | Winter | 260/249.6 |

FOREIGN PATENTS OR APPLICATIONS 49-81111  8/1974  Japan

Primary Examiner—John M. Ford
Attorney, Agent, or Firm—Lynn T. Fletcher; B. Woodrow Wyatt

[57] ABSTRACT

Fluorans useful as color precursors, particularly in the art of carbonless duplicating are normally colorless and are represented by the structural formula

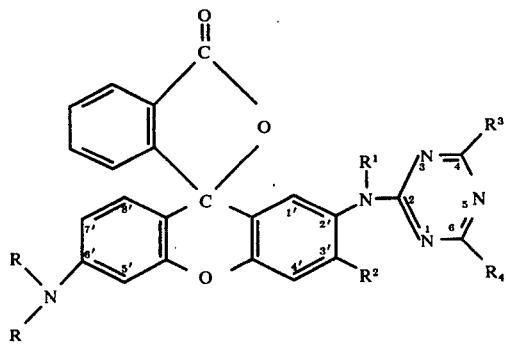

wherein R represents non-tertiary alkyl of one to four carbon atoms; $R^1$ and $R^2$ represent hydrogen or non-tertiary alkyl of one to four carbon atoms; $R^3$ and $R^4$ represent chlorine, $NH_2$ or one of the groups $-NR^5$-(lower-alkylene)-$N(R^6)(R^7)$, $-NR^5$-(lower-alkylene-$N^+(R^8)(R^9)(R^{10})$ An, $-NR^5$(lower-alkylene)-OH, $-NR^5$-(lower-alkylene)

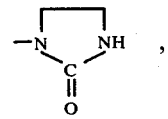

$-NR^5$-$(HSO_3$-$C_6H_4)$ or $-O$-(lower-alkylene)-$N(R^8)(R^9)$ in which $R^5$, $R^6$ and $R^7$ represent hydrogen or non-tertiary alkyl of one to four carbon atoms; $R^8$ and $R^9$ represent non-tertiary alkyl of one to four carbon atoms; $R^{10}$ represents non-tertiary alkyl of one to four carbon atoms, benzyl or benzyl substituted in the benzene ring by one or two of halo or alkyl of one to three carbon atoms; and An represents an anion.

22 Claims, No Drawings

2'-(4,6-DISUBSTITUTED)-s-TRIAZIN-2-YL)AMINO-6'-DIALKYLAMINO FLURANS

BACKGROUND OF THE INVENTION a. Field of the Invention

This invention relates to 2'-(4,6-disubstituted-s-triazin-2-yl)amino-6'-dialkylaminofluorans useful as color precursors, particularly in the art of carbonless duplicating systems as, for example, pressure sensitive and thermal systems and to processes for preparing said 2'-triazinyl-amino-substituted-6'-dialkylaminofluorans.

b. Description of the Prior Art

Several classes of organic compounds of widely diverse structural types are known to be useful as colorless precursors for carbonless duplicating systems. Among the more important classes, there may be named phenothiazines, for example, benzoyl leuco methylene blue; phthalides, for example, crystal violet lactone; fluorans, for example, 2'-anilino-6'-diethylaminofluoran and 2'-dibenzylamino-6'-diethylaminofluoran; and various other types of colorless precursors currently employed in commercially accepted carbonless copy systems. Moriga and Oda (Univ. Kyoto, Japan) in Kogyo Kaguka Zasshi 67 (7), 1054-8 (1964) [Chemical Abstracts 62: 2852a (1965)] describe the preparation and properties of a 3,3-bis(4-dimethylaminophenyl)phthalide which is substituted in the benzene ring of the phthalide moiety by a 4,6-dichloro-s-triazin-2-ylamino group. The compound is described as producing a green image when developed on bentonite in a simulated carbonless duplicating application. However, this prior art compound exhibits a number of deficiencies when employed in such a system which render it generally unsuitable for application in commercially feasible copy systems in light of the industry's standards for colorless precursors. Thus, its rate of color formation, upon contact with an electron withdrawing media such as an acidic clay or phenolic resin has been found to be rather slow. The intensity of tinctorial strength of the developed color produced by the reference compound has been found to be less than that generally found economically acceptable in the art when used within the concentrations usually employed in carbonless copy systems. Further, the solubility of the prior art compound in solvents regularly used in the copy system art for dissolving the dyes for microencapsulation is below that generally required to provide sufficient concentration of the dye to obtain satisfactory tinctorial strength in the developed form. Possibly the most important deficiency of the phthalide of Moriga and Oda is the low susceptibility to copiability of their color-developed form in standard copying machines, for example, a Xerox copier. By contrast, the compounds of this invention have been found to overcome the deficiencies of the prior art compound in that they proved to have a rapid rate of color formation on contact with acidic developing media; they have a good to excellent tinctorial strength to weight ratio; they are satisfactorily soluble in the usual microencapsulating solvents; and their developed color form is highly copiable in duplicating machines.

PRIOR PUBLICATION

Japanese Patent Publication No. Sho 49-81111, which was published on Aug. 5, 1974, describes a series of compounds having the formula

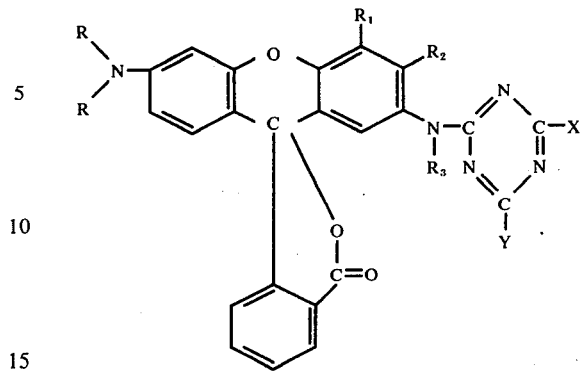

wherein R represents a lower-alkyl group; $R_1$ and $R_2$ represent a hydrogen atom, a lower-alkyl group or an alkoxy group; $R_3$ represents a hydrogen atom or a lower-alkyl group; and X and Y represent a chlorine atom, an alkoxy group or a residue of a primary or secondary amine. The compounds are disclosed in the reference as having utility as colorless precursors in carbonless, pressure-sensitive and thermal copy systems. This reference appeared subsequent to applicant's invention described herein and less than one year prior to the filing date of this application.

SUMMARY OF THE INVENTION

In one of its composition of matter aspects, the invention relates to certain 2'-(4-$R^3$-6-$R^4$-s-triazin-2-yl)$NR^1$-3'-$R^2$-6'-N(R)$_2$fluorans which are final products useful as colorless precursors in carbonless duplicating systems.

In a second composition of matter aspect, the invention relates to certain 2'-(4,6-dichloro-s-triazin-2-yl)$NR^1$-3'-$R^2$-6'-N(R)$_2$fluorans which, in addition to having the same utility as the final products, are useful as intermediates for the preparation of other final products of the invention.

In one of its process aspects, the invention relates to a process for preparing the 2'-(4,6-dichloro-s-triazin-2-yl)-$NR^1$-3'-$R^2$-6'-N(R)$_2$fluorans which comprises interacting the appropriate 2'-$NHR^1$-3'-$R^2$-6'-N(R)$_2$fluoran with cyanuric chloride.

In a second of its process aspects, the invention relates to a process for preparing the 2'-(4,6-diamino-s-triazin-2-yl)$NR^1$-3'-$R^2$-6'-N(R)$_2$fluorans which comprises interacting the appropriate 2'-$NHR^1$-3'-$R^2$-6'-N(R)$_2$fluoran with 2-chloro-4,6-diamino-1,3,5-triazine.

In a third of its process aspects, the invention relates to a process for preparing the 2'-(4-$R^3$-6-$R^4$-s-triazin-2-yl)$NR^1$-3'-$R^2$-6'-N(R)$_2$fluorans wherein one of $R^3$ or $R^4$ is a substituted amino group which comprises interacting the appropriate 2'-(4,6-dichloro-s-triazin-2-yl)$NR^1$-3'-$R^2$-6'-N(R)$_2$fluoran with approximately one molecular proportion of the appropriate substituted amine.

In a fourth of its process aspects, the invention relates to a process for preparing the 2'-(4-$R^3$-6-$R^4$-s-triazin-2-yl)$NR^1$-3'-$R^2$-6'-N(R)$_2$fluorans wherein each of $R^3$ and $R^4$ is a substituted amino group which comprises interacting the appropriate 2'-(4,6-dichloro-s-triazin-2-yl)$NR^1$-3'-$R^2$-6'-N(R)$_2$fluoran with approximately two molecular proportions of the appropriate amine.

In a fifth of its process aspects, the invention relates to a process for the preparation of a quaternary ammonium salt of a 2'-(4-$R^3$-6-$R^4$-s-triazin-2-yl)$NR^1$-3'-$R^2$-

6'-N(R)₂fluoran in which one or both of R³ and R⁴ are substituted amino groups having within the substituting group a quaternizable nitrogen atom which comprises interacting the appropriate said basic amino compound with an appropriate quaternizing agent, for example, benzyl chloride.

DETAILED DESCRIPTION INCLUSIVE OF THE PREFERRED EMBODIMENTS

More specifically, this invention, in its composition of matter aspect, resides in the novel 2'-(4-$R^3$-6-$R^4$-s-triazin-2-yl)$NR^1$-3'-$R^2$-6'-N(R)₂fluorans, which are useful as colorless precursors in the art of carbonless duplicating, and which are represented by the structural formula

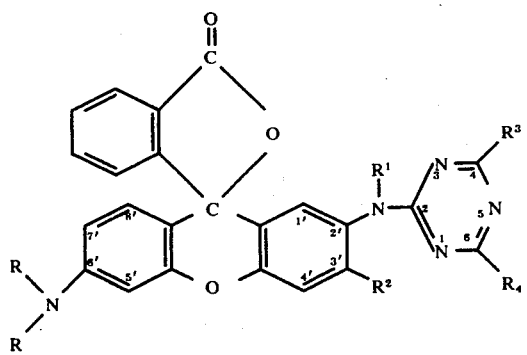

where R represents non-tertiary alkyl of one to four carbon atoms; $R^1$ and $R^2$ represent hydrogen or non-tertiary alkyl of one to four carbon atoms; $R^3$ and $R^4$ represent chlorine, NH₂ or one of the groups

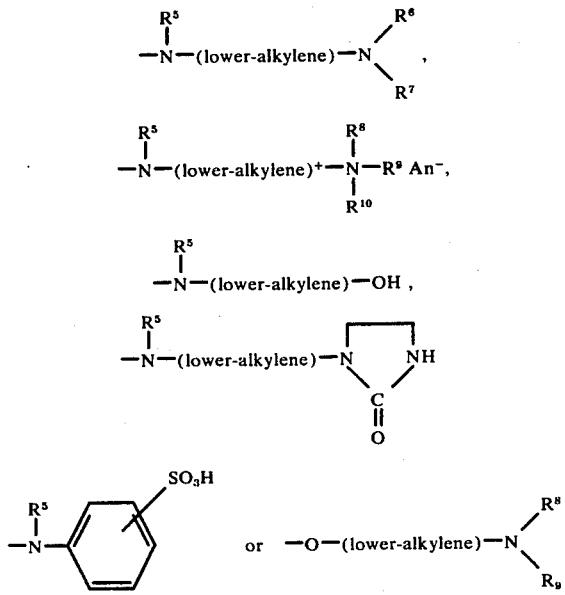

in which $R^5$, $R^6$ and $R^7$ represent hydrogen or non-tertiary alkyl of one to four carbon atoms; $R^8$ and $R^9$ represent non-tertiary alkyl of one to four carbon atoms; $R^{10}$ represents non-tertiary alkyl of one to four carbon atoms, benzyl or benzyl substituted in the benzene ring by one or two of halo or alkyl of one to three carbon atoms; and An represents an anion.

In the first particular embodiment in accordance with its composition of matter aspect, the invention sought to be patented resides in the novel 2'-(4,6-dichloro-s-triazin-2-yl)-$NR^1$-3'-$R^2$-6'-N(R)₂fluorans of Formula I wherein $R^3$ and $R^4$ are each chlorine and R, $R^1$ and $R^2$ each have the same respective meanings indicated in relation to Formula I.

In a second particular embodiment in accordance with its composition of matter aspect, the invention sought to be patented resides in the novel 2'-(4,6-diamino-s-triazin-2-yl)-$NR^1$-3'-$R^2$-6'-N(R)₂fluorans of Formula I wherein $R^3$ and $R^4$ are each NH₂ and R, $R^1$ and $R^2$ each have the same respective meanings indicated in relation to Formula I.

In a third particular embodiment in accordance with its composition of matter aspect, the invention sought to be patented resides in the novel 2'-(4-$R^3$-6-$R^4$-s-triazin-2-yl)$NR^1$-3'-$R^2$-6'-N(R)₂fluorans of Formula I in which $R^3$ is chlorine and $R^4$ is -$NR^5$-(lower-alkylene)-N($R^6$)($R^7$) and R, $R^1$, $R^2$, $R^5$, $R^6$ and $R^7$ each have the same respective meanings given in relation to Formula I.

In a fourth particular embodiment in accordance with its composition of matter aspect, the invention sought to be patented resides in the novel 2'-(4-$R^3$-6-$R^4$-s-triazin-2-yl)$NR^1$-3'-$R^2$-6'-N(R)₂fluorans of Formula I in which $R^3$ is chlorine and $R^4$ is

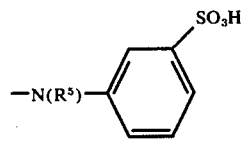

and R, $R^1$, $R^2$ and $R^5$ each have the same respective meanings indicated in relation to Formula I.

In a fifth particular embodiment in accordance with its composition of matter aspect, the invention sought to be patented resides in the novel 2'-(4-$R^3$-6-$R^4$-s-triazin-2-yl)$NR^1$-3'-$R^2$-6'-N(R)₂fluorans of Formula I where $R^3$ and $R^4$ are each —O-(lower-alkylene)-N($R^6$)($R^7$) and R, $R^1$, $R^2$, $R^6$ and $R^7$ each have the same respective meanings given in relation to Formula I.

In a sixth particular embodiment in accordance with its composition of matter aspect, the invention sought to be patented resides in the novel 2'-(4-$R^3$-6-$R^4$-s-triazin-2-yl)$NR^1$-3'-$R^2$-6'-N(R)₂fluorans of Formula I where $R^3$ and $R^4$ are each —$NR^5$-(lower-alkylene)-N($R^6$)($R^7$) and R, $R^1$, $R^2$, $R^5$, $R^6$ and $R^7$ each have the same respective meanings indicated in relation to Formula I.

In a seventh particular embodiment in accordance with its composition of matter aspect, the invention sought to be patented resides in the novel 2'-(4-$R^3$-6-$R^4$-s-triazin-2-yl)$NR^1$-3'-$R^2$-6'-N(R)₂fluorans of Formula I in which $R^3$ and $R^4$ are each —$NR^5$-(lower-alkylene)-$N^+$($R^8$)($R^9$)($R^{10}$) An⁻ and R, $R^1$, $R^2$, $R^5$, $R^8$, $R^9$, $R^{10}$ and An each have the same respective meanings given in relation to Formula I.

In an eighth particular embodiment in accordance with its composition of matter aspect, the invention sought to be patented resides in the novel 2'-(4-$R^3$-6-$R^4$-s-triazin-2-yl)$NR^1$-3'-$R^2$-6'-N(R)₂fluorans of Formula I where $R^3$ and $R^4$ are each —$NR^5$-(lower-alkylene)-OH and R, $R^1$, $R^2$ and $R^5$ each have the same respective meanings indicated in relation to Formula I.

In a ninth particular embodiment in accordance with its composition of matter aspect, the invention sought to be patented resides in the novel 2'-(4-$R^3$-6-$R^4$-s-triazin-2-yl)$NR^1$-3'-$R^2$-6'-N(R)₂fluorans of Formula I in which $R^3$ and $R^4$ are each —$NR^5$-(lower-alkylene)

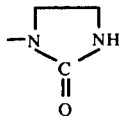

and R, $R^1$, $R^2$ and $R^5$ each have the same respective meanings given in relation to Formula I.

In one of its process aspects, the invention sought to be patented resides in the process for the preparation of the novel 2'-s-triazin-2-ylamino-6'-dialkylaminofluorans represented by Formula I in which $R^3$ and $R^4$ are each chlorine which comprises interacting an appropriate 2'-$NHR^1$-3'-$R^2$-6'-$N(R)_2$fluoran with approximately one molecular proportion of cyanuric chloride wherein R, $R^1$ and $R^2$ each have the same respective meanings given in relation to Formula I.

In a second process aspect, the invention sought to be patented resides in the process for the preparation of the novel 2'-s-triazin-2-ylamino-6'-dialkylaminofluorans represented by Formula I in which $R^3$ and $R^4$ are each $NH_2$ which comprises interacting an appropriate 2'-$NHR^1$-3'-$R^2$-6'-$N(R)_2$fluoran with approximately one molecular proportion of 2-chloro-4,6-diamino-1,3,5-triazine wherein R, $R^1$ and $R^2$ each have the same respective meanings indicated in Formula I.

In a third process aspect, the invention sought to be patented resides in the process for the preparation of the novel 2'-s-triazin-2-ylamino-6'-dialkylaminofluorans represented by Formula I in which $R^3$ is chlorine and $R^4$ is -$NR^5$-(lower-alkylene)-$N(R^6)(R^7)$ which comprises interacting an appropriate 2'-(4,6-dichloro-s-triazin-2-yl)$NR^1$-3'-$R^2$-6'-$N(R)_2$fluoran with approximately one molecular proportion of a compound having the formula $NHR^5$-(lower-alkylene)-$N(R^6)(R^7)$ wherein R, $R^1$, $R^2$, $R^5$, $R^6$ and $R^7$ each have the same respective meanings given in Formula I.

In a fourth process aspect, the invention sought to be patented resides in the process for the preparation of the novel 2'-s-triazin-2-ylamino-6'-dialkylaminofluorans represented by Formula I in which $R^3$ is chlorine and $R^4$ is —$NR^5$-(3-$HSO_3$-$C_6H_4$) which comprises interacting in a first step cyanuric chloride with approximately one molecular proportion of $NHR^5$-(3-$HSO_3$-$C_6H_4$) and interacting in the second step the 2,4-dichloro-6-[$NR^5$-(3-$HSO_3$-$C_6H_4$)]-1,3,5-triazine thus obtained with approximately one molecular proportion of an appropriate 2'-$NHR^1$-3'-$R^2$-6'-$N(R)_2$-fluoran wherein R, $R^1$ and $R^5$ each have the same respective meanings indicated in Formula I.

In a fifth process aspect, the invention sought to be patented resides in the process for the preparation of the novel 2'-s-triazin-2-ylamino-6'-dialkylaminofluorans represented by Formula I in which $R^3$ and $R^4$ are each -O-(lower-alkylene)-$N(R^6)(R^7)$ which comprises interacting an appropriate 2'-(4,6-dichloro-s-triazin-2-yl)$NR^1$-3'-$R^2$-6'-$N(R)_2$fluoran with approximately two molecular proportions of a compound having the formula HO-(lower-alkylene-$N(R^6)(R^7)$ wherein R, $R^1$, $R^2$, $R^6$ and $R^7$ each have the same respective meanings given in Formula I.

In a sixth process aspect, the invention sought to be patented resides in the process for the preparation of the novel 2'-s-triazin-2-ylamino-6'-dialkylaminofluorans represented by Formula I in which $R^3$ and $R^4$ are each —$NR^5$-(lower-alkylene)-$N(R^6)(R^7)$ which comprises interacting an appropriate 2'-(4,6-dichloro-s-triazin-2-yl)($NR^1$-3'-$R^2$-6'-$N(R)_2$fluoran with approximately two molecular proportions of a compound having the formula $NHR^5$-(lower-alkylene)-$N(R^6)(R^7)$ wherein R, $R^1$, $R^2$, $R^5$, $R^6$ and $R^7$ each have the same respective meanings indicated in Formula I.

In a seventh process aspect, the invention sought to be patented resides in the process for the preparation of the novel 2'-s-triazin-2-ylamino-6'-dialkylaminofluorans represented by Formula I in which $R^3$ and $R^4$ are each —$NR^5$-(lower-alkylene)-$N^+(R^8)(R^9)(R^{10})$ $An^-$ which comprises interacting a compound represented by Formula I in which $R^3$ and $R^4$ are each -$NR^5$-(loweralkylene)-$N(R^6)(R^7)$ in which $R^6$ and $R^7$ are each non-tertiary alkyl of one to four carbon atoms with either an alkyl halide, a benzyl halide or benzyl halide substituted in the benzene ring by one or two of halo or alkyl of one to three carbon atoms and wherein R, $R^1$, $R^2$, $R^5$, $R^8$, $R^9$, $R^{10}$ and An each have the same respective meanings given in Formula I.

In an eighth process aspect, the invention sought to be patented resides in the process for the preparation of the novel 2'-s-triazin-2-ylamino-6'-dialkylaminofluorans represented by Formula I in which $R^3$ and $R^4$ are each -$NR^5$-(lower-alkylene)-OH which comprises interacting an appropriate 2'-(4,6-dichloro-s-triazin-2-yl)$NR^1$-3'-$R^2$-6'-$N(R)_2$fluoran with approximately two molecular proportions of a compound having the formula $NHR^5$-(lower-alkylene)-OH wherein R, $R^1$, $R^2$ and $R^5$ each have the same respective meanings indicated in Formula I.

In a ninth process aspect, the invention sought to be patented resides in the process for the preparation of the novel 2'-s-triazin-2-ylamino-6'-dialkylaminofluorans represented by Formula I in which $R^3$ and $R^4$ are each —$NR^5$(lower-alkylene)-

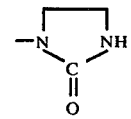

which comprises interacting an appropriate 2'-(4,6-dichloro-s-triazin-2-yl)$NR^1$-3'-$R^2$-6'-$N(R)_2$fluoran with approximately two molecular proportions of a compound having the formula

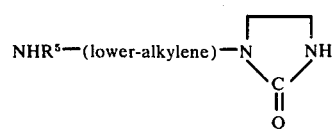

wherein R, $R^1$, $R^2$ and $R^5$ each have the same respective meanings given in Formula I.

As used herein, the term "halo" includes bromo, chloro, fluoro and iodo. Similarly, the term "halide" includes bromide, chloride, fluoride and iodide.

As used herein, the term "non-tertiary alkyl" means saturated, aliphatic hydrocarbon groups, either straight or branched-chain, containing from one to four carbon atoms, and includes methyl, ethyl, propyl, isopropyl, butyl and isobutyl.

As used throughout, the term "(lower-alkylene)" means a divalent saturated straight or branched-chain aliphatic radical of from two to five carbon atoms having valence bonds attached to different carbon atoms. Thus, radicals represented by the term "(lower-alkylene)" are, for example $—CH_2CH_2—$, $—CH_2CH_2CH_2—$, $—(CH_2)_4—$, $—(CH_2)_5—$, $—CH(CH_3)CH_2—$, $—CH_2—CH_2—CH(CH_3)—CH_2—$, $—CH_2—CH(C_2H_5)—CH_2—$, and the like.

As used herein, the term "An" represents Anion. By Anion is meant any monovalent ion derived from an organic or inorganic acid, H Anion, by removal of an acidic hydrogen ion. Exemplary anions are, halide, hydroxy, alkanoate, nitrate, phosphate, alkylsulfate and arylsulfate. Other monovalent anions are found in the literature, for example, Hackh's Chemical Dictionary, 3rd Edition (1946) at pages 12–13, and Chemical Abstracts Vol. 56, Nomenclature, at pages 72n–80n, both incorporated herein by specific reference thereto. As is known, one anion can be changed to another anion by use of conventional ion exchange methods. The halides, i.e., chloride, bromide, fluoride and iodide and in particular chloride and bromide are particularly preferred as the anions for the colorless precursors of this invention because of the generally ready availability of the quaternizing agents containing them. However, the scope of the compounds herein described and claimed is in no way to be thereto restricted.

The novel compounds represented by Formula I above are essentially colorless in the depicted lactone form. When contacted with an acidic medium, for example, silica gel, or one of the types regularly employed in carbonless duplicating systems, for example, silton clay or phenolic resins, they readily develop a colored image of good to excellent tinctorial strength. Moreover, it has been found that when the compounds of Formula I are intimately mixed with an acidic developer of the type generally employed in thermal papers, that is papers which produce a colored image when contacted with a heated stylus or heated type, for example, bisphenol A, heating of the mixture produces a red-colored material. It has also been found that when the compounds of this invention are converted to a water-soluble form, the essentially colorless water-soluble compound is substantive to cellulose, for example, paper.

The rapid development of color on contact of the compounds of Formula I with silica gel, silton clay or a phenolic resin demonstrates that they are highly suitable for use as colorless precursors in pressure-sensitive carbonless duplicating systems. Their ability to readily form a deep color when heated in admixture with an acidic developer such as bisphenol A, makes them useful in thermal paper marking systems, either where an original or a duplicate copy is prepared by contacting the thermal paper with a heated stylus or heated type in any of the methods generally known in the art. The substantivity to cellulose of the water-soluble forms of the compounds of Formula I makes them effective for dyeing paper. The dyed paper then may be used for producing images as originals by contacting with an ink containing an acidic developing substance. Moreover, the dyed paper may be used in a pressure-sensitive system in which it is contacted with a matching sheet coated with microencapsulated acidic developing substance.

As stated above, the compounds of Formula I are useful as color precursors, particularly in the art of carbonless duplicating systems. As with other colorless precursors currently in use in the art, the compounds are colorless under neutral or basic conditions, but become colored when contacted with an acidic material such as silica gel, a phenolic resin or an acidic clay. It is frequently desired that the images produced by such color precursors be copiable by xerographic means. A widely used color precursor is 3,3-bis(4-dimethylaminophenyl)-6-dimethylaminophthalide, or, as this compound has been more simply designated, crystal violet lactone. Crystal violet lactone produces a blue image which has the advantage of being intense but which suffers the disadvantage of being poorly copiable by xerographic means. To counteract this disadvantage, other color precursors have been mixed with crystal violet lactone as described, for example, in U.S. Pat. No. 3,525,630. The images produced by the compounds of Formula I, although generally less intense in color than images produced by crystal violet lactone, are readily copiable by xerographic means. For this reason, the difficulties inherent in using mixed color precursors to achieve xerographic copiability can be avoided by using a compound of Formula I alone.

The best mode contemplated by the inventor of carrying out this invention will now be described as to enable any person skilled in the art to which it pertains to make and use the same.

The compounds represented by Formula I wherein $R^3$ and $R^4$ are each chlorine have dual utilities in that they are useful as final products of the invention having the same utility as colorless precursors and they are also intermediates to those final products of Formula I wherein one or both of $R^3$ and $R^4$ represent a substituted amino moiety of the type depicted in relation to Formula I. The compounds in which $R^3$ and $R^4$ are each chlorine are prepared by interacting the appropriate 2'-$R^1$-amino-3'-$R^2$-6'-dialkylaminofluoran with approximately an equimolar quantity of cyanuric chloride. The reaction is advantageously carried out in a mixed solvent system consisting of aprotic and/or protic solvents and in the presence of sufficient aqueous sodium hydroxide solution to neutralize the hydrochloric acid generated in the reaction. A particularly preferred solvent system is acetone:p-dioxane. The reaction can be carried out at a temperature in the range of 0° to 30° C, but preferably at a temperature in the range of 0° to 5° C. The 2'-(4,6-dichloro-s-triazin-2-yl)$R^1$amino-3'-$R^2$-6'-dialkylaminofluoran thus obtained is isolated by filtration followed by washing with an inert organic solvent, for example, benzene and then dried. Alternatively, when the dichlorotriazinyl product is to be utilized as an intermediate to other products represented by Formula I, it is unnecessary to isolate the product and the slurry containing the intermediate may be used directly.

The compounds represented by Formula I wherein $R^3$ and $R^4$ are each $NH_2$ are conveniently prepared by interacting the appropriate 2'-$R^1$amino-3'-$R^2$-6'-dialkylaminofluoran with approximately an equimolar quantity of 2-chloro-4,6-diamino-1,3,5-triazine in the presence of a strong mineral acid, for example, hydrochloric acid. The reaction is advantageously carried out in an aqueous medium at reflux temperature, that is, at a temperature in the range of 95° to 100° C. The product is isolated by neutralization of the cooled reaction mixture with a dilute aqueous solution of a base, for example, five percent aqueous sodium hydroxide solution. The product is then collected and subjected to recrystallization from a suitable organic solvent. A particularly preferred recrystallization solvent is chloroform.

The 2'-$R^1$amino-3'-$R^2$-6'-dialkylaminofluorans required for the preparation of the compounds of Formula I in which $R^3$ and $R^4$ are each chlorine or $NH_2$ are known compounds. Cyanuric chloride and 2-chloro-4,6-diamino-1,3,5-triazine are both known compounds and both are commercially available.

The compounds of Formula I wherein one or both of $R^3$ and $R^4$ are one of the groups -$NR^5$-(lower-alkylene)-$N(R^6)(R^7)$, —$NR^5$-(lower-alkylene)-OH, -O-(lower-alkylene)-$N(R^8(R^9)$ or —$NR^5$-(lower-alkylene)

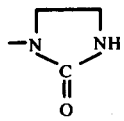

are each prepared by essentially the same general procedure. Thus, the appropriate 2'-(4,6-dichloro-s-triazin-2-yl)($R^1$amino-3'-$R^2$-6'-dialkylaminofluoran is interacted with the appropriate dialkylaminoalkylamine, hydroxyalkylamine, dialkylaminoalkanol or 1-(aminoalkyl)imidazolidine-2-one. When it is desired to prepare a monosubstituted compound, approximately one molecular proportion of the side "side chain" is employed and when it is desired to obtain a disubstituted compound, approximately two molecular proportions of the "side chain" is employed. The reaction is conveniently carried out in a solvent mixture consisting of aprotic and/or protic solvents, for example, a mixture of p-dioxane and acetone in the presence of sufficient alkali to absorb the hydrochloric acid generated at a temperature in the range of 60° to 90° C, preferably at the reflux temperature of the solvent mixture. Although the reaction can be run by dissolving the appropriate 2'(4,6-dichloro-s-triazin-2-yl)$R^1$amino-3'-$R^2$-6'-dialkylaminofluoran in the solvent system, it is generally satisfactory and preferred to use this intermediate as obtained in its own reaction mixture without prior isolation. The desired mono-or disubstituted triazinylfluoran is isolated from its reaction mixture by evaporating the solvent and dissolving the residue in chloroform or benzene. The product is then reprecipitated by the addition of hexane or ligroin.

The compounds of Formula I in which one or both of $R^3$ and $R^4$ are an aminobenzenesulfonic acid (or alternatively and equivalently the alkali metal or ammonium salt thereof) are conveniently prepared by first interacting the appropriate aminobenzenesulfonic acid, that is, orthanilic, metanilic or sulfanilic acid with cyanuric chloride. When it is desired to effect monosubstitution, approximately one molecular proportion of the aminobenzenesulfonic acid is employed and the reaction is carried out at a temperature in the range of 0° to 5° C. When it is desired to effect disubstitution, approximately two molecular proportions are employed and the reaction is carried out at a temperature in the range of 20° to 40° C. The reaction is advantageously carried out in an aqueous medium in the presence of a base, for example, sodium bicarbonate. A particularly suitable reaction medium is a water/acetone mixture. The thus obtained 2-chloro-. 1,3,5-triazine substituted by one or two aminobenzenesulfonic acid groups is then, without isolation and in the same reaction medium, interacted with approximately one molecular proportion of the appropriate 2'-$R^1$amino-3'-$R^2$-6'-dialkylaminofluoran in the presence of sufficient alkali to absorb the hydrochloric acid generated and if desired to form the alkali metal salt of the sulfonic acid group or groups present in the molecule. This latter condensation is initiated at 0° to 5° C and the temprature is gradually raised to the reflux temperature of the solvent system (50° to 100° C) where it is maintained for several hours. The product can optionally be isolated either in the form of the free acid or in the form of an alkali metal or ammonium salt depending on whether the product is desired for dyeing application involving a water-soluble salt form or for an application in which a non-water-soluble (free acid) form is desired, for example, microencapsulation.

The quaternary ammonium compounds of Formula I wherein one or both of $R^3$ and $R^4$ represent the group —$NR^5$-(lower-alkylene)-$N^+(R^8)(R^9)(R^{10})$ $An^-$ are prepared by interacting an appropriate compound represented by Formula I in which one or both of $R^3$ and $R^4$ are —$NR^5$-(lower-alkylene)-$N(R^6)(R^7$ with an alkyl halide or a substituted or unsubstituted benzyl halide. The quaternization is conveniently carried out either with or without solvent. Suitable solvents are to be found among polar and non-polar solvents. Among these may be mentioned the lower-alkanols, for example, isopropyl alcohol; aromatic hydrocarbons, for example, benzene and toluene; ketones, for example, acetone; and acylnitriles, for example, acetonitrile. The reaction is generally carried out at the reflux temperature of the chosen solvent system and is in the range of 60° to 100° C. Illustrative of the alkyl halides useful for this conversion are, for example, methyl chloride, ethyl bromide and butyl chloride. Benzyl halides useful for the conversion are, for example, benzyl chloride, o-chlorobenzyl chloride, benzyl bromide, 2,5-dimethylbenzyl chloride, 4-bromobenzyl bromide, benzyl iodide, 3,4-dichlorobenzyl chloride, 3-fluorobenzyl chloride and the like.

The reactive amine and hydroxy intermediates required for interaction with the appropriate 2'-(4,6-dichloro-s-triazin-2-yl)$R^1$N-3'-$R^2$-6'-dialkylaminofluoran to obtain the compounds of Formula I are known compounds whose preparation is well-known in the prior art. The following compounds are exemplary of these reactive amine and hydroxy compounds useful in the practice of this invention.

3-Dimethylaminopropylamine,
3-Dimethylaminopropanol,
3-Diethylaminopropylamine,
Monoethanolamine,
1-(2-aminoethyl)imidazolidine-2-one,
2-Dimethylaminoethylamine,
N-methyl-ethanolamine,
4-Diethylaminobutylamine,
5-Diethylaminopentylamine,
2-Diethylaminoethanol,
3-Dimethylaminopropanol,
2-Dimethylaminoethanol,
3-Dibutylaminopropanol,
2-Dibutylaminoethanol,
2-Diisopropylaminoethylamine, 3-Dibutylaminopropylamine,
Ethylenediamine,
2-Diethylaminoethylamine,
4-Diethylamino-1-methyl-butylamine,
  Orthanilic acid,
  Metanilic acid, and
  N-Methylsulfanilic acid.

The molecular structures of the compounds of the invention were assigned on the basis of the modes of synthesis and study of their infrared, ultraviolet and NMR spectra.

The following examples will further illustrate the invention without, however, limiting it thereto. All melting points are uncorrected.

EXAMPLE 1

A mixture of 2.0 g of 2'-amino-6'-diethylaminofluoran and 70.0 ml of toluene was warmed to 50° C to effect solution and then cooled to 0° C by means of an ice/salt bath. The temperature was maintained in the range of 0° to 5° C while, during a period of one hour, a solution of 0.90 g of cyanuric chloride in 40.0 ml of toluene as gradually added. An ice-cold solution of 0.4 g of sodium hydroxide in 40 g of water was then slowly added to the reaction mixture while maintaining the internal temperature in the range of 0° to 5° C by means of external cooling. After stirring for one hour at 0° to 5° C, the resulting slurry was filtered. The solid remaining on the funnel was reslurried in 200 ml of benzene for ten minutes, collected by filtration, and dried to constant weight in vacuo at 60° C. The product represented by Formula I in which R is $C_2H_5$; $R^1$ and $R^2$ are each hydrogen; and $R^3$ and $R^4$ are each Cl did not melt up to 290° C. An acetone solution of the product spotted on silica gel, a phenolic resin or an acidic clay, develops an orange-red color.

EXAMPLE 2

A mixture of 25.0 ml of distilled water, 0.96 g of 2'-amino-6'-diethylaminofluoran and 0.40 g of 2-chloro-4,6-diamino-1,3,5-triazine was heated at reflux for a period of fifteen minutes. There was then added 0.90 g of ten percent aqueous hydrochloric acid and reflux was maintained for a period of one hour. The reaction was cooled slightly and an additional 0.90 g portion of ten percent aqueous hydrochloric acid was added. The reaction mixture was then heated at reflux for a period of forty-five minutes. The mixture was allowed to coo to approximately 25° C and sufficient five percent aqueous sodium hydroxide solution was added to render the mixture alkaline to Brilliant Yellow test paper. The solid which formed was separated by filtration, washed with water and air dried at 60° C. The dried product was slurried in benzene, filtered and the operation repeated. The residual solid was dissolved in 100 ml of chloroform at 50° C and the solution clarified by filtration through diatomaceous earth. The filtrate was then evaporated to a volume of approximately 50 ml and cooled to 20° C. The solid which separated was collected by filtration and dried at 60° C in vacuo to obtain the compound represented by Formula I in which R is $C_2H_5$; $R^1$ and $R^2$ are each hydrogen; and $R^3$ and $R^4$ are each $NH_2$ as a light pink colored crystalline solid which melted at 287°–288° C. A chloroform solution of the product spotted on silica gel, a phenolic resin or an acidic clay, develops a red color.

EXAMPLE 3

A mixture of 3.86 g of 2'-amino-6'-diethylaminofluoran, 38.0 g of p-dioxane and 38.0 g of acetone was cooled to 0° C by means of an ice/salt bath. The internal temperature was maintained in the range of 0° to 5° C while there was added to the reaction mixture during a period of five minutes, 3.60 ml of a ten percent aqueous sodium hydroxide solution. This was followed by the addition during a period of forty-five minutes of a solution of 1.82 g of cyanuric chloride in 15.0 ml of p-dioxane. There was then added during a period of thirty minutes at an internal temperature in the range of 0° to 5° C, a solution of 3.06 g of 3-dimethylaminopropylamine in 10.0 ml of acetone. The reaction mixture was gradually warmed to gentle reflux, which was continued for approximately four hours. The resulting solution was set aside at room temperature, overnight. The solvent was evaporated at reduced pressure leaving a tarry, semi-solid residue. The residue was dissolved in 400 ml of benzene and the solution concentrated by evaporation to approximately 200 ml total volume. The solution was chilled to 10° C and n-hexane slowly added. A gray-colored solid separated which was collected by filtration and dried in vacuo at 60° C to yield 5.5 g of the product represented by Formula I in which R is $C_2H_5$; $R^1$ and $R^2$ are each hydrogen; and $R^3$ and $R^4$ are each $-NH-(CH_2CH_2CH_2)-N(CH_3)_2$. A benzene solution of the product, which melted over the range 145°–198° C, develops a red color when spotted on silica gel, a phenolic resin or an acidic clay.

EXAMPLE 4

A mixture of 14.6 g of 2'-[4,6-bis(3-dimethylaminopropylamino)-s-triazin-2-yl]-amino-6'-diethylaminofluoran (the product described in Example 3), 201 ml of p-dioxane and 53 ml of acetone was warmed to 40° C. There was then added to the mixture during a period of one-half hour a solution of 2.78 g of benzyl chloride in 10.0 ml of toluene. The reaction mixture was heated to 80° C and maintained at that temperature for a period of two hours at the end of which an additional 0.3 g of benzyl chloride was added. Heating at 80° C was continued for an additional period of two hours. Upon cooling, a tar-like ball formed and some precipitated solid was observed in the reaction mixture. The solvent was distilled away under reduced pressure. During the removal of the solvent, the tar-like material gradually gave away to an amorphous solid. The solid was triturated successively with n-hexane and diethyl ether and was then dried at 60° C in vacuo to obtain 17.0 g of the product represented by Formula I in which R is $C_2H_5$; $R^1$ and $R^2$ are each hydrogen; $R^3$ is $NH-(CH_2-CH_2CH_2)-N^+(CH_3)_2(CH_2C_6H_5)$; $R^4$ is $NH-(CH_2CH_2CH_2)-N(CH_3)_2$; and An is Cl. The solid began to sublime at 149° C and melted at 200° C with decomposition. An acetone solution of the product when spotted on silica gel, a phenolic resin or an acidic clay, develops a red color.

EXAMPLE 5

A mixture of 1.66 g of 2'-(4,6-bis[3-dimethylaminopropylamino]-s-triazin-2-yl)amino-6'-diethylaminofluoran, 150 ml of acetonitrile and 1.27 g of benzyl chloride was stirred at gentle reflux overnight (approximately seventeen hours). The resulting solution was concentrated by evaporation of the acetonitrile at atmospheric pressure. The semi-crystalline residue was ground in a mortar and air dried. There was thus obtained the product represented by Formula I in which R is $C_2H_5$; $R^1$ and $R^2$ are each hydrogen; $R^3$ and $R^4$ are each $NH-(CH_2-CH_2CH_2)$ $-N^+(CH_3)_2(CH_2C_6H_5)$; and An is Cl as a water-soluble solid. A water solution of the product when spotted on silica gel, a phenolic resin or an acidic clay, develops a red color.

EXAMPLE 6

A solution of 1.27 g of metanilic acid dissolved in 10.0 ml of water as combined with 60 g of acetone and the mixture cooled to 0° C by means of an ice/salt bath. Then, 0.42 g of sodium bicarbonate and 0.91 g of cyanuric chloride were added and the reaction mixture was stirred for a period of one hour at 0° to 5° C. To the reaction mixture there was then added 1.93 g of 2'-amino-6'-diethylaminofluoran and the resulting reaction mass was allowed to warm to 20° C at which time 0.50 g of sodium carbonate was added. The resultant slurry was stirred for forty-five minutes at approximately 30° C. An additional 1.27 g portion of metanilic acid was then added and the reaction mixture was heated at reflux (approximately 60° C) for two hours. Approximately 50 ml of solvent was distilled from the reaction flask and replaced with 50 ml of p-dioxane. The resulting solution was heated at reflux (approximately 78° C) for seventeen hours and then cooled. Then, 0.25 g of sodium carbonate was added and the reaction mixture was heated to distill away the solvent to just short of dryness. The residual solid was slurried in a mixture of acetone and benzene and the solvent mixture then evaporated in a fume hood at ambient temperature. The product which is thus obtained and is represented by Formula I in which R is $C_2H_5$; $R^1$ and $R^2$ are each hydrogen; $R^3$ is Cl; and $R^4$ is $NH-(3-NaSO_3-C_6H_4)$, softens at 89° C and partially sublimes at 99° C, but does not completely melt below 300° C. A water solution of the product when spotted on silica gel, a phenolic resin or an acidic clay, develops a red color.

EXAMPLE 7

Proceeding in a manner similar to that described in Example 3 above, 2'-(4,6-dichloro-s-triazin-2-ylamino-6'-diethylaminofluoran (represented by Formula I where R is $-C_2H_5$; $R^1$ and $R^2$ are each hydrogen; and $R^3$ and $R^4$ are each Cl) was prepared by the interaction of 2'-amino-6'-diethylaminofluoran with cyanuric chloride and then without isolation, was interacted in situ with approximately two molecular proportions of 3-dimethylamino-propanol to obtain the product represented by Formula I where R is $C_2H_5$; $R^1$ and $R^2$ are each hydrogen; and $R^3$ and $R^4$ are each $-O-(CH_2CH_2CH_2)-N(CH_3)_2$ as a pink-colored amorphous solid having a melting point range of 110°–165° C. An acetone solution of this product when spotted on silica gel, a phenolic resin or an acidic clay, develops a red color.

EXAMPLE 8

Following the procedure described in Example 3 above, 2'-(4,6-dichloro-s-triazin-2-yl)amino-6'-diethylaminofluoran (Formula I: R is $-C_2H_5$; $R^1$ and $R^2$ are each hydrogen; and $R^3$ and $R^4$ are each Cl) was prepared by the interaction of 2'-amino-6'-diethylaminofluoran with cyanuric chloride and then without isolation was interacted in situ with approximately two molecular proportions of 3-diethylamino-propylamine to obtain 3.10 g of the product represented by Formula I where R is $-C_2H_5$; $R^1$ and $R^2$ are each hydrogen; $R^3$ and $R^4$ are each $-NH-(CH_2CH_2CH_2)-N(C_2H_5)_2$ as a pink-colored amorphous solid. An acetone solution of this product spotted on silica gel, a phenolic resin or an acidic clay, develops a red color.

EXAMPLE 9

Proceeding in a manner similar to that described in Example 3 above, 2'-(4,6-dichloro-s-triazin-2-yl)amino-6'-diethylaminofluoran (Formula I: R is $-C_2H_5$; $R_1$ and $R_2$ are each hydrogen; and $R_3$ and $R_4$ are each Cl) was prepared by interacting 2'-amino-6'-diethylaminofluoran with cyanuric chloride. The product was then interacted in situ with approximately two molecular proportions of monoethanol amine to obtain the product represented by Formula I where R is $-C_2H_5$; $R_1$ and $R_2$ are each hydrogen; and $R_3$ and $R_4$ are each $-NH-(CH_2CH_2)-OH$ as a pink-colored amorphous solid. An acetone solution of this product spotted on silica gel, a phenolic resin or an acidic clay, develops a red color.

EXAMPLE 10

Following the procedure described in Example 3 above, 2'-(4,6dichloro-s-triazin-2yl)amino-6'-diethylaminofluoran (Formula I: R is $-C_2H_5$; $R^1$ and $R^2$ are each hydrogen; and $R^3$ and $R^4$ are each Cl) obtained by interacting 2'-amino-6'-diethylaminofluoran with cyanuric chloride, was without prior isolation interacted in situ with approximately two molecular proportions of 1-(2-aminoethyl)imidazolidine-2-one to obtain the product represented by Formula I where R is $-C_2H_5$; $R^1$ and $R^2$ are each hydrogen; and $R^3$ and $R^4$ are each $-NH-(CH_2CH_2)$

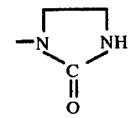

as a dark pink colored amorphous solid. An acetone solution of this product when spotted on silica gel, a phenolic resin or an acidic clay, develops a red color.

EXAMPLE 11

Proceeding in a manner similar to that described in Example 3 above, 2'-(4,6-dichloro-s-triazin-2yl)amino-6'-diethylaminofluoran (Formula I: R is $-C_2H_5$; $R^1$ and $R^2$ are each hydrogen; and $R^3$ and $R^4$ are each Cl) was prepared by the interaction of 2'-amino-6'-diethylaminofluoran with cyanuric chloride. The product was not isolated but was interacted in situ with approximately one molecular proportion of 3-dimethylaminopropylamine with stirring at 0°–5° C to obtain the product represented by Formula I where R is $-C_2H_5$; $R^1$ and $R^2$ are each hydrogen; $R^3$ is Cl; and $R^4$ is $-NH-(CH_2CH_2CH_2)-N(CH_3)_2$ as a dark pink-colored amorphous solid. An acetone solution of this product when spotted on silica gel, a phenolic resin or an acidic clay, develops a red color.

EXAMPLE 12

Following the procedure described in Example 3 above, 2'-(4,6-dichloro-s-triazin-2yl)amino-6'-diethylaminofluoran (Formula I: R is $-C_2H_5$; $R^1$ and $R^2$ are each hydrogen; and $R^3$ and $R^4$ are each Cl) was prepared by interaction of 2'-amino-6'-diethylaminofluoran with cyanuric chloride and was without prior isolation interacted in situ with approximately two mocolor when contacted with silica gel, a phenolic resin or acidic clay, were prepared or can be prepared

| Example | R | R¹ | R² | R³ | R⁴ |
|---------|---|----|----|----|----|
| 13 | $C_2H_5$ | H | H | Cl | $N(CH_3)CH_2CH_2OH$ |
| 14 | $C_2H_5$ | H | H | $N(CH_3)CH_2CH_2OH$ | $N(CH_3)CH_2CH_2OH$ |
| 15 | $C_3H_7$ | H | $C_2H_5$ | $NH(CH_2)_4N(C_2H_5)_2$ | $NH(CH_2)_4N(C_2H_5)_2$ |
| 16 | $C_2H_5$ | $CH_3$ | H | $NH(CH_2)_5N(C_2H_5)_2$ | $NH(CH_2)_5N(C_2H_5)_2$ |
| 17 | $C_2H_5$ | H | $CH_3$ | $N(CH_3)(CH_2)_2OH$ | $N(CH_3)(CH_2)_2OH$ |
| 18 | $CH_3$ | n-$C_4H_9$ | $CH_3$ | $NH(CH_2)_2OH$ | $NH(CH_2)_2OH$ |
| 19 | $C_4H_9$ | H | H | $O(CH_2)_2N(C_2H_5)_2$ | $O(CH_2)_2N(C_2H_5)_2$ |
| 20 | $CH_3$ | H | sec-$C_4H_9$ | $O(CH_2)_3N(CH_3)_2$ | $O(CH_2)_2N(CH_3)_2$ |
| 21 | $C_3H_7$ | H | n-$C_4H_9$ | $O(CH_2)_2N(CH_3)_2$ | $O(CH_2)_2N(CH_3)_2$ |
| 22 | $CH_3$ | sec-$C_4H_9$ | $C_3H_7$ | $O(CH_2)_3N(C_4H_9)_2$ | $O(CH_2)_3N(C_4H_9)_2$ |
| 23 | $C_2H_5$ | H | $C_2H_5$ | $O(CH_2)_2N(C_4H_9)_2$ | $O(CH_2)_2N(C_4H_9)_2$ |
| 24 | $CH_3$ | $C_2H_5$ | $CH_3$ | $NH(CH_2)_2N(i-C_3H_7)_2$ | $NH(CH_2)_2N(i-C_3H_7)_2$ |
| 25 | $C_2H_5$ | H | H | $NH(CH_2)_3N(n-C_4H_9)_2$ | $NH(CH_2)_3N(n-C_4H_9)_2$ |
| 26 | $C_2H_5$ | $C_3H_7$ | H | $NH(CH_2)_2NH_2$ | $NH(CH_2)_2NH_2$ |
| 27 | $C_2H_5$ | H | H | $NH(CH_2)_2N(C_2H_5)_2$ | $NH(CH_2)_2N(C_2H_5)_2$ |
| 28 | $C_3H_7$ | H | H | $\overset{+}{NH(CH_2)_3N(CH_3)_2}-(C_6H_5CH_2)$ Br⁻ | $\overset{+}{NH(CH_2)_3N(CH_3)_2}-(C_6H_5CH_2)$ Br⁻ |
| 29 | $CH_3$ | H | $C_3H_7$ | $NH(CH_2)_5N(C_2H_5)_2$ | $NH(CH_2)_5N(C_2H_5)_2$ |
| 30 | $C_2H_5$ | H | H | $NHCH(CH_3)(CH_2)_3-N(C_2H_5)_2$ | $NHCH(CH_3)(CH_2)_3-N(C_2H_5)_2$ |
| 31 | $CH_3$ | $CH_3$ | H | $\overset{+}{NH(CH_2)_2N(CH_3)_2}-(2-Cl-C_6H_4CH_2)$ Cl⁻ | $NH(CH_2)_2N(CH_3)_2$ |
| 32 | $C_2H_5$ | H | H | $NH(CH_2)_3N(C_2H_5)_2$ | $\overset{+}{NH(CH_2)_3N(C_2H_5)_2}-(2,5-(CH_3)_2-C_6H_3CH_2)$ Cl⁻ |
| 33 | $CH_3$ | H | $CH_3$ | $NH(CH_2)_3N(CH_3)_2$ | $\overset{+}{NH(CH_2)_3N(CH_3)_2}-(4-Br-C_6H_4CH_2)$ Br⁻ |
| 34 | $C_3H_7$ | H | H | $NH(CH_2)_5N(C_2H_5)_2$ | $\overset{+}{NH(CH_2)_5N(C_2H_5)_2}-(C_6H_5CH_2)$ I⁻ |
| 35 | $C_2H_5$ | H | $C_2H_5$ | $\overset{+}{NH(CH_2)_3N(CH_3)_2}-(2-F-C_6H_4CH_2)$ Cl⁻ | $\overset{+}{N(CH_2)_3N(CH_3)_2}-(2-F-C_6H_4CH_2)$ Cl⁻ |
| 36 | $CH_3$ | n-$C_4H_9$ | H | $NH(CH_2)_2N(C_2H_5)_2$ | $\overset{+}{NH(CH_2)_2N(C_2H_5)_2}-(3,4-Cl_2-C_6H_3CH_2)$ Cl⁻ |
| 37 | $C_2H_5$ | H | $CH_3$ | $NH(CH_2)_3N(CH_3)_2$ | $\overset{+}{NH(CH_2)_3N(CH_3)_2}-(3,4-(CH_3)_2-C_6H_3CH_2)$ Cl⁻ |
| 38 | $C_2H_5$ | H | H | $NH(CH_2)_4(C_2H_5)_2$ | $\overset{+}{NH(CH_2)_4N(C_2H_5)_2}-(3-F-C_6H_4CH_2)$ Cl⁻ |
| 39 | $CH_3$ | H | $CH_3$ | $NH(CH_2)_3N(CH_3)_2$ | $\overset{+}{NH(CH_2)_3N(CH_3)_2}-(2,4-Cl_2-C_6H_3CH_2)$ Cl⁻ |
| 40 | $C_2H_5$ | H | H | $NH(CH_2)_3N(C_2H_5)_2$ | $\overset{+}{NH(CH_2)_3N(C_2H_5)_2}-(3-Br-C_6H_4CH_2)$ Br⁻ |
| 41 | $C_2H_5$ | H | $CH_3$ | $\overset{+}{NH(CH_2)_2N(CH_3)_2}-(2-CH_3-C_6H_4CH_2)$ Cl⁻ | $\overset{+}{NH(CH_2)_2N(CH_3)_2}-(2-CH_3-C_6H_4CH_2)$ Cl⁻ |
| 42 | $CH_3$ | H | H | $\overset{+}{NH(CH_2)_2N(C_2H_5)_2}-(CH_3)$ Cl⁻ | $\overset{+}{NH(CH_2)_2N(C_2H_5)_2}-(CH_3)$ Cl⁻ |
| 43 | $C_2H_5$ | $C_3H_7$ | H | $NH(CH_2)_3N(C_4H_9)_2$ | $\overset{+}{NH(CH_2)_3N(C_4H_9)_3}$ Br⁻ |
| 44 | $C_2H_5$ | H | $CH_3$ | $NH(CH_2)_5N(C_2H_5)_2$ | $\overset{+}{NH(CH_2)_5N(C_2H_5)_3}$ I⁻ |
| 45 | $CH_3$ | H | $CH_3$ | $\overset{+}{NH(CH_2)_2N(CH_3)_2}-(C_3H_7)$ Br⁻ | $\overset{+}{NH(CH_2)_2N(CH_3)_2}-(C_3H_7)$ Br⁻ |
| 46 | $C_2H_5$ | H | H | Cl | $NH(2-SO_3H-C_6H_4)$ |
| 47 | $C_3H_7$ | H | H | Cl | $N(CH_3)(4-SO_3H-C_6H_4)$ | lecular proportions of 2-dimethylamino-ethylamine to obtain the product represented by Formula I where R is —$C_2H_5$; R¹ and R² are each hydrogen; and R³ and R⁴ are each —NH-($CH_2CH_2$)-N($CH_3$)₂ as a pink-colored amorphous solid. An acetone solution of this product when spotted on silica gel, a phenolic resin or an acidic clay, develops a red color.

Proceeding by methods similar to those described in the foregoing examples, the following additional colorless precursor 2'-(4-R³-6R⁴-s-triazin-2-yl)NR¹-3'-R²-6'-N(R)₂fluorans of Formula I, which develop to a red

EXAMPLE 48

The utility of the compounds described in the foregoing examples as color forming components in thermal copying systems was demonstrated as follows. A portion of the product of Example 3 (Formula I: R is $C_2H_5$; R¹ and R² are each hydrogen; and R³ and R⁴ are each NH-($CH_2$)₃-N($CH_3$)₂) and an equal weight of bisphenol A were intimately mixed. A thin layer of the pinkish-white-colored powder mixture was then spread on a white porcelain tile and heated to approximately 140° C at which temperature the mixture developed a deep red color.

EXAMPLE 49

Hand sheets dyed with the compound of Example 5 above (Formula I: R is $C_2H_5$; $R^1$ and $R^2$ are each hydrogen; and $R^3$ and $R^4$ are each $NH$-$(CH_2)_3$-$N^+(CH_3)_2(CH_2C_6H_5)Cl^-$) were prepared by adding a 0.5 percent aqueous solution of the compound to an aqueous slurry of a cellulosic pulp (bleached Kraft fiber). The dyestuff was exhausted onto the fiber and the sheets formed on a laboratory sheet mold. The sheet was pressed between blotting paper in a hydraulic press and then air dried. When the paper thus prepared was streaked with a toluene solution of a phenolic resin, a deep red-colored image was formed.

I claim:
1. A compound having the formula

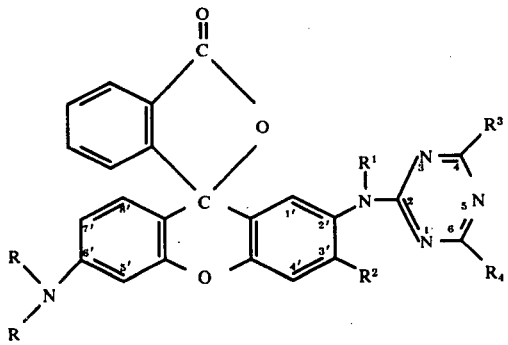

where R represents non-tertiary alkyl of one to four carbon atoms; $R^1$ and $R^2$ represent hydrogen or non-tertiary alkyl of one to four carbon atoms; $R^3$ and $R^4$ represent chlorine, $NH_2$ or one of the groups

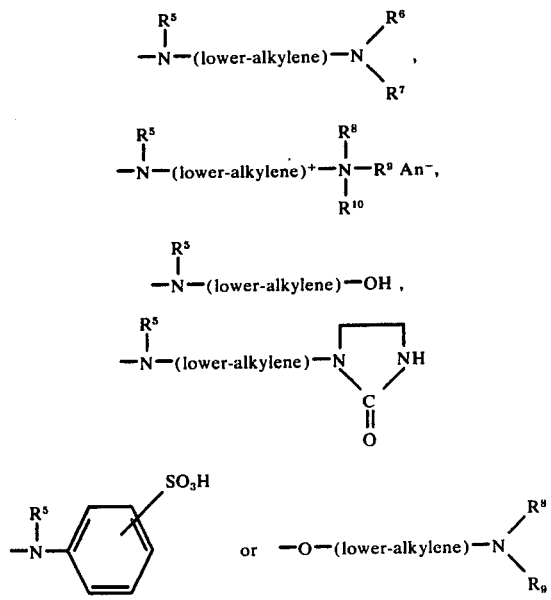

in which $R^5$, $R^6$ and $R^7$ represent hydrogen or non-tertiary alkyl of one to four carbon atoms; $R^8$ and $R^9$ represent non-tertiary alkyl of one to four carbon atoms; $R^{10}$ represents non-tertiary alkyl of one to four carbon atoms, benzyl or benzyl substituted in the benzene ring by one or two of halo or alkyl of one to three carbon atoms; and An represents an anion selected from the group consisting of halides, hydroxy, alkanoates, nitrate, phosphate, alkylsulfates and arylsulfates.

2. A compound according to claim 1 where $R^3$ and $R^4$ are each chlorine and R, $R^1$ and $R^2$ each have the same respective meanings given in claim 1.

3. The compound according to claim 2 where R is ethyl; and $R^1$ and $R^2$ are each hydrogen.

4. A compound according to claim 1 where $R^3$ and $R^4$ are each $NH_2$ and R, $R^1$ and $R^2$ each have the same respective meanings given in claim 1.

5. The compound according to claim 4 where R is ethyl; and $R^1$ and $R^2$ are each hydrogen.

6. A compound according to claim 1 where $R^3$ is chlorine; and $R^4$ is —$NR^5$-(lower-alkylene)-$N(R^6)(R^7)$ and R, $R^1$, $R^2$, $R^5$, $R^6$ and $R^7$ each have the same respective meanings given in claim 1.

7. The compound according to claim 6 where R is ethyl; $R^1$, $R^2$ and $R^5$ are each hydrogen; $R^6$ and $R^7$ are each methyl; and lower-alkylene is 1,3-propylene.

8. A compound according to claim 1 where $R^3$ is chlorine; and $R^4$ is and R, $R^1$, $R^2$ and $R^5$ each have the same respective meanings given in claim 1.

9. The compound according to claim 8 where R is ethyl; and $R^1$, $R^2$ and $R^5$ are each hydrogen.

10. A compound according to claim 1 where $R^3$ and $R^4$ are each —O-(lower-alkylene)-$N(R^6)(R^7)$ and R, $R^1$, $R^2$, $R^6$ and $R^7$ each have the same respective meanings given in claim 1.

11. The compound according to claim 10 where R is ethyl; $R^1$ and $R^2$ are each hydrogen; $R^6$ and $R^7$ are each methyl; and loweralkylene is 1,3-propylene.

12. A compound according to claim 1 where $R^3$ and $R^4$ are each —$NR^5$-(lower-alkylene)-$N(R^6)(R^7)$ and R, $R^1$, $R^2$, $R^5$, $R^6$ and $R^7$ each have the same respective meanings given in claim 1.

13. The compound according to claim 12 where R is ethyl; $R^1$, $R^2$ and $R^5$ are each hydrogen; $R^6$ and $R^7$ are each methyl; and lower-alkylene is 1,2-ethylene.

14. The compound according to claim 12 where R is ethyl; $R^1$, $R^2$ and $R^5$ are each hydrogen; $R^6$ and $R^7$ are each methyl; and lower-alkylene is 1,3-propylene.

15. The compound according to claim 12 where R, $R^6$ and $R^7$ are each ethyl; $R^1$, $R^2$ and $R^5$ are each hydrogen; and lower-alkylene is 1,3-propylene.

16. A compound according to claim 1 where $R^3$ and $R^4$ are each —$NR^5$-(lower-alkylene)-$N^+(R^8)(R^9)(R^{10})$ An$^-$ and R, $R^1$, $R^2$, $R^5$, $R^8$, $R^9$, $R^{10}$ and An each have the same respective meanings given in claim 1.

17. The compound according to claim 16 where R is ethyl; $R^1$, $R^2$ and $R^5$ are each hydrogen; $R^8$ and $R^9$ are each methyl; $R^{10}$ is benzyl; and lower-alkylene is 1,3-propylene.

18. A compound according to claim 1 where $R^3$ and $R^4$ are each —$NR^5$-(lower-alkylene)-OH and R, $R^1$, $R^2$ and $R^5$ each have the same respective meanings given in claim 1.

19. The compound according to claim 18 where R is ethyl; $R^1$, $R^2$ and $R^5$ are each hydrogen; and lower-alkylene is 1,2-ethylene.

20. The compound according to claim 18 where R is ethyl; $R^1$ and $R^2$ are each hydrogen; $R^5$ is methyl and lower-alkylene is 1,2-ethylene.

21. A compound according to claim 1 where $R^3$ and $R^4$ are each -$NR^5$ -(lower-alkylene)

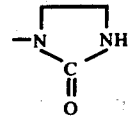

and R, $R^1$, $R^2$ and $R^5$ each have the same respective meanings given in claim 1.

22. The compound according to claim 21 where R is ethyl; $R^1$, $R^2$ and $R^5$ are each hydrogen; and lower-alkylene is 1,2-ethylene.

* * * * *